United States Patent [19]

Skladnev et al.

[11] Patent Number: 5,792,053

[45] Date of Patent: Aug. 11, 1998

[54] HYBRID PROBE FOR TISSUE TYPE RECOGNITION

[75] Inventors: Victor N. Skladnev, Vaucluse; Richard N. Thompson, Killarney Heights, both of Australia; Irwin Wunderman, Mountain View, Calif.; David J. Bull, Epping, Australia

[73] Assignee: Polartechnics, Limited, Sydney, Australia

[21] Appl. No.: 818,912

[22] Filed: Mar. 17, 1997

[51] Int. Cl.⁶ .................................................. A61B 5/00
[52] U.S. Cl. ........................... 600/407; 600/475; 600/477
[58] Field of Search .................................. 600/309, 310, 600/407, 473, 475–477

[56] References Cited

U.S. PATENT DOCUMENTS

| | | | |
|---|---|---|---|
| 3,647,299 | 3/1972 | Lavallee | 356/41 |
| 3,910,701 | 10/1975 | Henderson et al. | 356/39 |
| 3,994,590 | 11/1976 | Di Martini et al. | 356/178 |
| 4,587,421 | 5/1986 | Robertson | 250/239 |
| 4,942,877 | 7/1990 | Sakai et al. | 128/633 |
| 5,036,853 | 8/1991 | Jeffcoat et al. | 128/634 |
| 5,188,108 | 2/1993 | Secker | 600/475 |
| 5,291,884 | 3/1994 | Heinemann et al. | 600/477 |
| 5,411,024 | 5/1995 | Thomas et al. | 128/634 |
| 5,427,093 | 6/1995 | Ogawa et al. | 128/633 |
| 5,456,260 | 10/1995 | Kollias et al. | 600/477 |
| 5,492,118 | 2/1996 | Gratton et al. | 600/477 |
| 5,520,177 | 5/1996 | Ogawa et al. | |
| 5,598,843 | 2/1997 | Caisey et al. | 600/476 |

OTHER PUBLICATIONS

Mendelson, Ph.D. et al., Design and Evaluation of a New Reflectance Pulse Oximeter Sensor, Medical Instrument, vol. 11, No. 4, pp. 187–173, 1988.

Neuman, M.R., In Medical Instrumentation: Application and Design, pp. 265–266, Webster, J.G. (ed) 2nd Ed. Boston Houghton Miffliin, 1992.

Primary Examiner—Ruth S. Smith
Attorney, Agent, or Firm—Gottlieb, Rackman & Reisman, P.C.

[57] ABSTRACT

A hybrid probe in which the optical pathway and the optical sensors comprise elements located within a compact hybrid chip structure. The full optical system of the hybrid probe is located at its tip. No fibers are required to bring the light to and from the tip of the probe. This is achieved in part by mounting one or more LED dice on a substrate at the probe tip. Appropriate connections are made to these dice which are powered from electronics in the handle of the probe.

13 Claims, 4 Drawing Sheets

HYBRID PROBE FOR TISSUE TYPE RECOGNITION

FIELD OF THE INVENTION

The present invention relates to probes and a method for identifying different tissue types including those displaying modifications involving pre-cancerous and cancerous stages, diseased tissue, and those that are in a transitional stage.

The identification of different tissue types is provided via a set of measurements of the tissue's physical properties and in particular the optical and electrical properties of the tissue.

BACKGROUND OF THE INVENTION

The medical profession often needs to have an objective assessment of the health of the tissue of a patient. The patient may have suffered tissue damage as a result of accidental or deliberate trauma as for example during a surgical operation. The patient may also be suffering some other more persistent irritation as a result, for example, of being confined to bed which can lead to bed sores. It is valuable for a medical practitioner to be able to tell in advance the type of treatment that would benefit the patient.

It is well known, for example, that early detection of tissues displaying pre-cancer or cancer modifications is important for successful medical treatment. We have already disclosed an apparatus and method for carrying out this detection. The invention described in this application represents a significant improvement on the apparatus disclosed in patent application Ser. No. 08/332,830, assigned to the same assignee as the current invention.

The previous disclosure described an apparatus that employed optical fibre technology for performing the optical measurements. While this technology is effective, a good deal of manual labor is involved in building a probe to that design. The level of skill required precludes the manufacture of the device on a large scale at a low price for a mass market.

The fibre-based device also has potential problems with temperature sensitivity which cannot be avoided with optical fibers, particularly when they are bent and the temperature sensitivity cannot readily be compensated.

Close spacing of opto-electronics components is typically avoided in diagnostic probe design because of the difficulties of providing adequate electrical and optical isolation. Optical fibers are often used to enable the opto-electronics components to be held remote from each other, from the working face of the probe and from the patient to achieve the required isolations. This invention overcomes these isolation problems while achieving the needed high resolution of measurement.

BRIEF SUMMARY OF THE INVENTION

The present invention concerns a hybrid probe for both electrical and optical measurements in which the optical pathway and the optical sensors comprise elements located within a hybrid chip structure that is compact.

This invention overcomes the problems inherent in earlier designs of probes by siting the opto-electronics components in a high density array at the working face of the probe. This is achieved by employing bare opto-electronic dice rather than packaged components and mounting these in close proximity to each other in an optimally designed chamber. Appropriate electrical connections are made to these dice which are powered from electronics in the handle of the probe.

According to one aspect of the present invention there is disclosed an apparatus for identifying different tissue types including those displaying modifications involving precancerous or cancerous activity, said apparatus comprising a probe having one end shaped to face said tissue and having at least one radiation source towards the end of the probe and a detector for that radiation and a comparator to compare the measured received radiation with known values to thereby identify the tissue type.

The apparatus may also include at least one electrode to apply electrical signals to the tissue and electrical means to measure the resulting electrical response by said tissue. A comparator is employed to compare the electrical and optical signals with a catalogue of known tissue type signals to identify the tissue.

One difficulty with such a configuration is the need to isolate light emitting and light receiving elements from one another. The hybrid probe is designed to examine areas of tissue having a diameter of the order of 2 mm, which requires that photodiode detectors be placed in close juxtaposition with light emitters yet optically isolated so that light signals do not pass directly from an emitter to a detector without intervention (i.e. backscattering) by the tissue under examination. This is accomplished in the present invention by the use of metal barriers. The metal barriers also shield the detector circuitry from electrical interference carried by current pulses that must be applied to the LEDs to induce them to emit light. The metal barrier may be left floating or grounded, but can also serve an additional role as an electrode for making electrical measurements to replace or supplement the two or three noble metal electrodes adjacent to the hybrid circuit normally used for the electrical measurements to be made on the tissue.

In addition the hybrid structure provides a preamplifier in close proximity to the photodiodes to amplify the small current from the photodiode detectors and feed it to the electronics in the handle of the probe and from there to the analysis circuitry.

It has been pointed out above that the fiber-based probe is temperature sensitive. This temperature sensitivity often occurs at bends in the fiber. It is often not practical to measure these temperatures so compensation is difficult to achieve. A change in temperature at the tip of the probe is likely to occur when the probe is brought into contact with the tissue of a warm blooded being. The subject of this invention overcomes the forms of temperature sensitivity arising from the fibers. The radiation output of LEDs is also temperature sensitive but for precise measurements can be compensated by using a characteristic of the LED to determine its own temperature. The bandgap potential of LEDs is a known function of temperature, allowing the temperature to be determined by applying a known current to the diode and measuring the potential across it. This can then be used to correct for the output of the LED using established equations thereby compensating for the changed radiation emission caused by temperature changes.

DETAILED DESCRIPTION OF PREFERRED EMBODIMENTS

To delineate the dimensions of a suspected area of abnormal tissue by the use of optical measurements to identify tissue types it is essential that the detector be able to resolve areas at a high resolution. The effective area that is illuminated by the radiation during the optical measurements therefore needs to be as small as possible, down to as little as one square millimeter. Below this dimension abnormalities are unlikely to affect the health of the patient since they will most likely spontaneously clear within a relatively short time.

To attain dimensions of this order it is necessary to crowd the opto-electronics into an extremely small volume. This places demands on the technology that is employed which were heretofore unachievable. It is a feature of this invention that we have accomplished packing densities that have not been achieved previously. The invention also provides effective devices where three or more electrodes are sited within the small dimensions of the assembly enabling electrical measurements to be made on essentially the same area of tissue as that measured optically. The invention provides a novel design layout solving these problems.

The layout described achieves the needed isolation of the input and output optical signals and the corresponding emitter driving currents from minuscule detector currents. This isolation is a critical requirement since the optical losses involved in this method of measurement are great and effective shielding is vital. The opportunity for signal leakage is ever present since the drive currents to the LEDs are many orders of magnitude greater than the detector currents. Isolation of the electrical measurements from the optical ones is conveniently achieved by performing the measurements sequentially but nearly simultaneously rather than precisely simultaneously.

The invention does not reside entirely in any particular layout. Other layouts of the components are feasible if the principles embodied in this invention are adhered to. These principles concern the isolation of elements and the maintaining of active elements in close, but suitably spaced proximity to the tissue under examination. These principles are described in part by the ends to be accomplished by suitable layouts and guidance is further given by specifying preferred layouts. For example the barrier can be used as an electrode for the purposes of tissue electrical measurements. By this means the electrical measurement can be placed in the center of the region of optical measurement, a desirable but not an essential feature.

Figure 1:
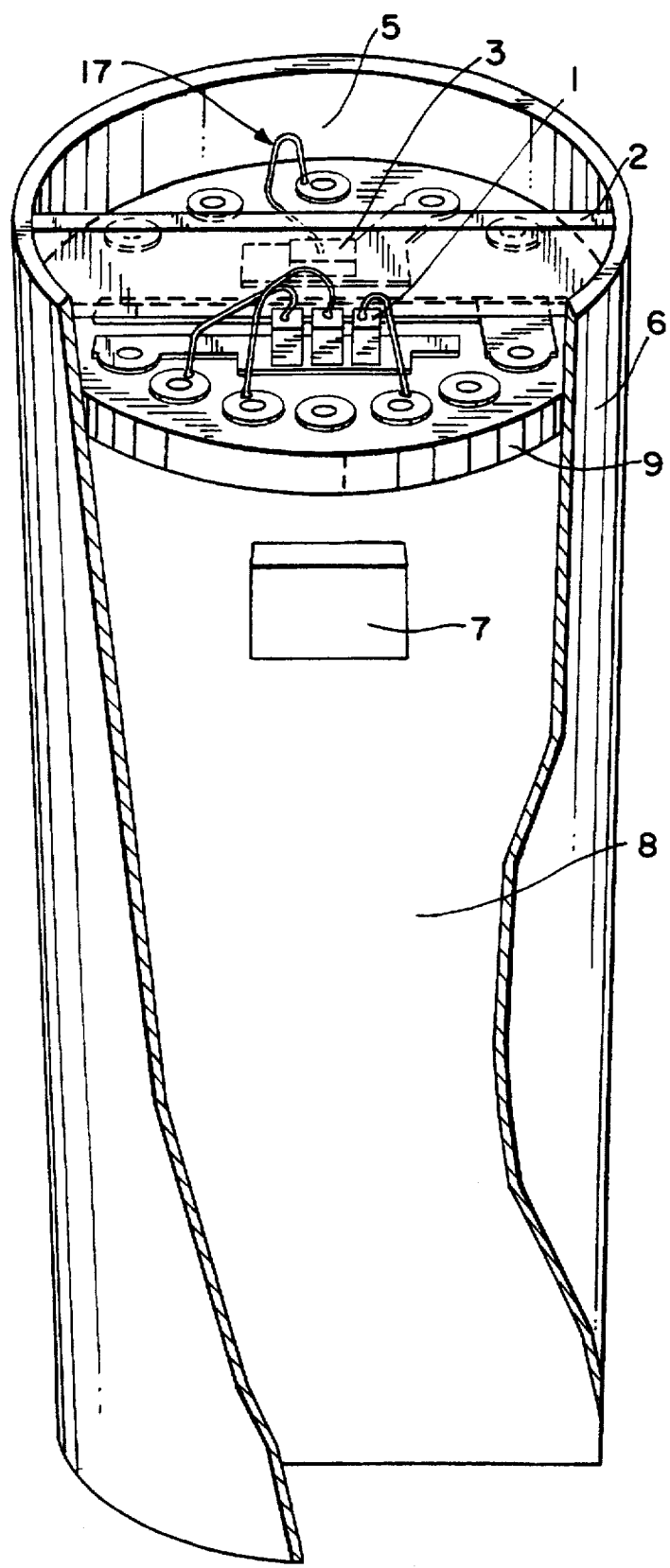
FIG. 1 is an illustration of the layout of the tip of the probe as seen in perspective showing only optical components.

FIG. 1 shows a perspective view of the probe tip with the placement of the opto-electronic components clearly shown. This probe is useful to detect the onset of precancer or cancer within the endocervical canal or os in addition to making measurements on the outer parts of the cervix. As shown the hybrid probe has a cylindrical shape with a diameter of about 3 mm. The radiation sources 1 in this case are LEDs and three are shown in this assembly, located within a space 5 at the tip of the probe. They are mounted on a substrate 9 along with the other components. To control the direction of the radiation and to act as an electrostatic shield the barrier 2 divides the assembly into two chambers. This barrier must be electrically conductive to provide the needed electrical shielding. It can be grounded or left floating. In the far side chamber is located the radiation detector 3.

Figure 2:
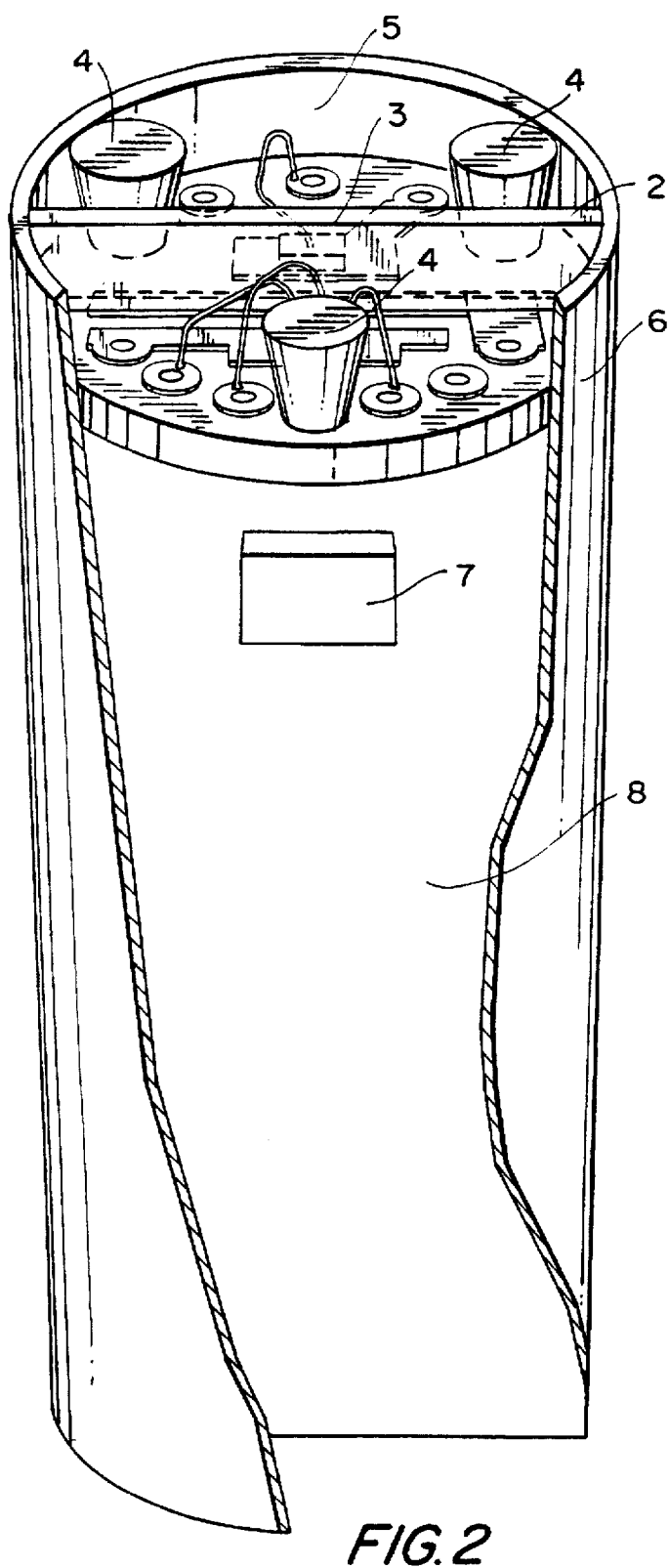
FIG. 2 is an illustration of another embodiment that includes electrodes in the probe tip.

FIG. 2 illustrates an embodiment of the invention that includes electrodes. In this embodiment electrodes 4 have been included in the assembly to enable electrical measurements to be made. Three are shown but the number can vary depending on other factors. The electrodes illustrated are circular but they may be of other dimensions. For example kidney-shaped electrodes offer advantages since they can be of greater area than by limiting the shape to circular. An advantage in adopting the kidney shape is to achieve the maximum possible electrode area without compromising the optical performance or the electrical resolution. Larger electrodes by their nature produce less noisy data because they are sampling a larger area of tissue which is naturally less variable than a smaller area. The space 5 is typically filled with a transparent resin to hold the components in position and to protect them from damage. The assembly is mounted in a tube 6 which forms part of the completed probe. An amplifier 7 boosts the signal from the detector 3 so that it can be conveyed back to the controller. The amplifier is mounted on a circuit board 8 which holds other circuits involved in driving the LEDs and electrodes. A critical feature of this arrangement arises from the need to take special care with the shielding of the wiring from the detector 3 to its amplifier 7. The currents flowing in this wire may be of the order of nanoamperes. The drive current to the nearby LEDs may be as high as 100 milliamperes. The ratio of these currents is huge so shielding is vital. In addition the patient's body may have substantial voltage signals present because of adjacent wiring or other electrical equipment being operated nearby. The detector circuit must therefore be shielded from this source of interference as well. This is achieved by the use, for example, of multilayer circuit boards 8 to convey the signals. The disposition of the signals flowing in the tracks on these boards must be chosen carefully to avoid unwanted capacitive or electromagnetic coupling.

The optical layout needs to be planned because of the conflicting demands made on it. The radiation signal reaching the tissue needs to reach a level sufficient to compete with the ambient light level being employed for the operator's visual needs. LEDs have limited light output so as much as possible of this output radiation needs to be available to illuminate the tissue. To achieve this the LEDs 1 are placed as close as possible to the tissue. If, in fact, the efficiency of LEDs continues to improve, the above consideration may become less of a problem in the future.

There are two limits to how small the distance from the top of the LEDs to the tissue can be made. The first of these is the need to accommodate the bond wires 17 from the top of the LEDs which tends to loop upward from the surface of the LED die. The second arises from optical considerations. It is important to control the direction and angle of the illumination of the tissue surface so that probes behave consistently. If the distance between the opto-electronics and the tissue varies, the sensitivity of the device will vary. Tissue recognition will thereby be impaired. The distance from the LEDs to the tissue surface should therefore be kept large enough that assembly tolerances do not lead to uncontrolled variability between probes. Since the position and size of the LED top surface can typically be controlled to within plus or minus 25 micrometers, this uncertainty should not be more than, say, 5% of the LED to surface distance. That distance should therefore be not less than 0.5 millimeter.

The lateral placement of the dice is similarly controllable to only 25 micrometers so this needs to be factored in to the geometric considerations. More deeply placed dice will be less sensitive to errors in placement.

The lateral placement also affects the diagnostic ability of the device by modifying the depth of penetration of the radiation prior to its return to the detector. It is important therefore that the placement be chosen to achieve the desired depth of penetration bearing in mind the tolerances on the accuracy that can be maintained. In general the closer the opto-electronics components 1 and 3 are to the barrier 2 the smaller the depth of penetration.

Figure 3:
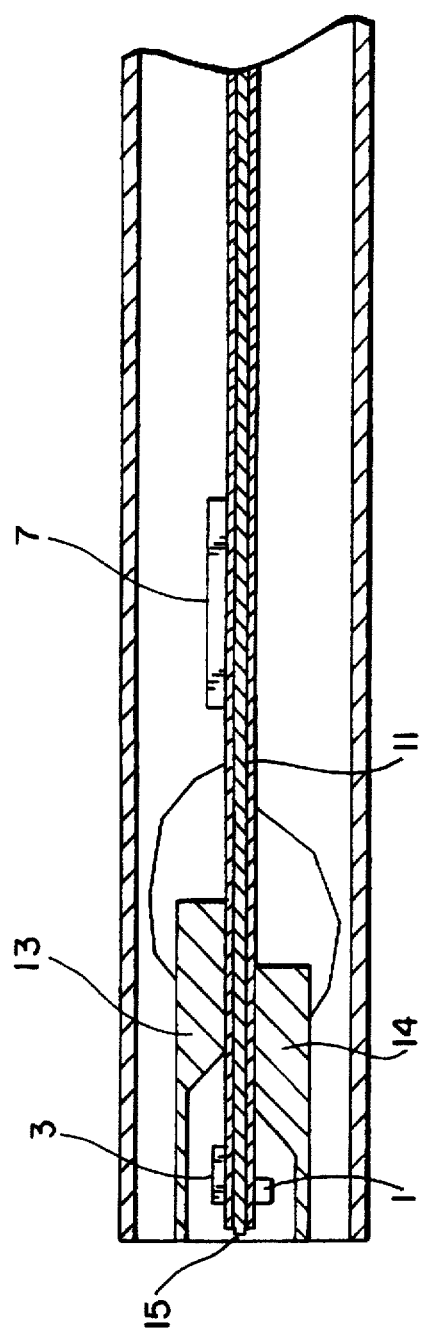
FIG. 3 is an illustration in section of another embodiment of the invention having a multilayered substrate running along at least a portion of the length of the probe.

FIG. 3 shows another embodiment of the invention. In this embodiment the optoelectronics components 1 and 3 are mounted on opposite sides of a multilayer PCB 11. The light emitters 1 are on one side while the detector 3 is on the other. The detector is connected to the amplifier 7 which is mounted back from the tip.

Figure 4:
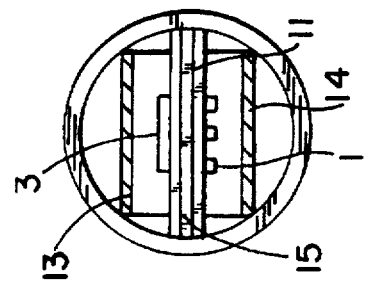
FIG. 4 is an end view of the multilayered substrate embodiment from the probe tip end.

Electrodes 13, 14 and 15 are situated around the opto-electronics and electrodes 13 and 14 perform the additional duty of acting as radiation reflectors respectively to direct the radiation to the tissue and thence back to the detector after is has been backscattered. FIG. 4 shows an end view of the same embodiment.

Figure 5:
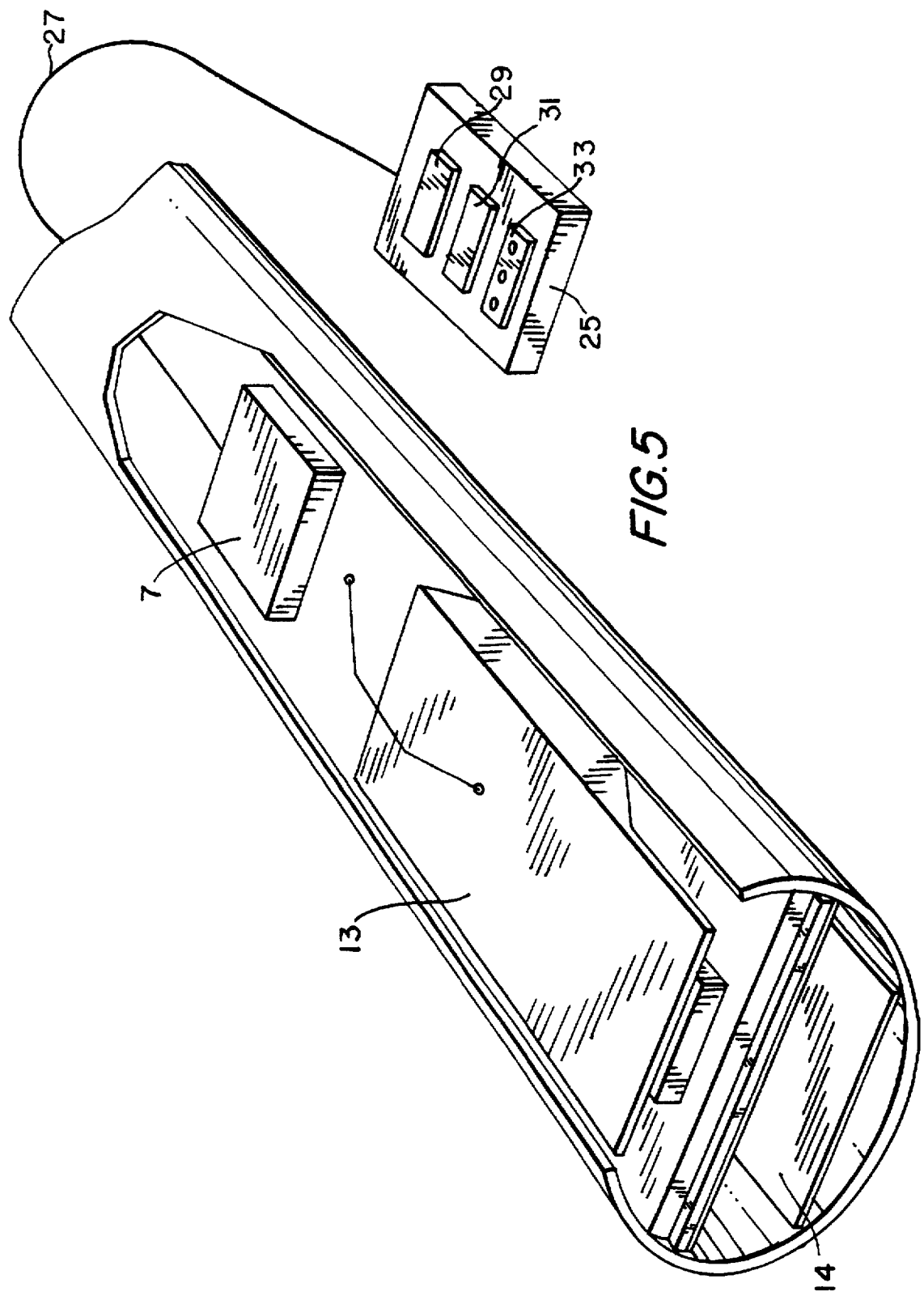
FIG. 5 is a perspective view of the multilayered substrate embodiment.

FIG. 5 shows a perspective view of the same embodiment. The controller 25, and may be remote from the probe tip, connected by appropriate wiring 27, drives the radiation sources and measures the signals from the detector and from the electrodes when they are included. It also applies a small current to the LEDs and measures the voltage drop to determine the temperature of the LEDs. It then calculates a correction for the radiation output from the LEDs and adjusts the measured values of the detector signal accordingly. The controller 25 comprises a processer 29, a comparater 31, and an indicater 33.

It is also possible to build the hybrid assembly into other forms such as a capsule with an extended lead. This enables the capsule to pass into internal organs such as the stomach or lungs. It could even be passed down thicker veins or arteries. An endoscopic type of mounting could be provided for the device.

The controller performs manipulations on the corrected signals from the probe and arrives at a decision as to the tissue type by comparing the data with a catalogue of data of known tissue types. The decision is then communicated to the operator via one of several means such as by means of colored lights on the probe, by an audible tone, or by a indicator 33 the controller 25.

Although the invention has been described in terms of preferred embodiments, it is intended that the protection afforded by this patent not be so limited, but be determined by the full valid extent of the following claims.

What is claimed is:

1. Apparatus for identifying tissue which is suspected of being physiologically changed, said apparatus comprising:
   a probe having a tip comprising a close packed array of components, said components comprising
      at least one emitter, each emitter comprising a light emitting die, said light emitting die configured to irradiate said tissue;
      at least one detector, each detector comprising a detector die, said detector die configured to receive that radiation after it has been backscattered by said tissue;
      a shield comprising an electrode for making electrical measurements on said tissue and sited between said at least one emitter and said at least one detector to prevent leakage of optical and electrical signals from one to the other;
   said apparatus further comprising
      a controller coupled to the at least one emitter and the at least one detector that supplies drive signals and receives responses, said controller comprising
         a processor for said responses in combination in order to categorize said tissue, and
         a comparator for comparing the categorization of said tissue with expected tissue types from a catalogue so as to identify said tissue, and
      an indicator arrangement for indicating to a user the tissue type identified.

2. The apparatus for identifying tissue of claim 1 wherein said electrode is configured to supply electrical signals to said tissue and to receive electrical responses from the tissue.

3. Apparatus for identifying tissue which is suspected of being physiologically changed, said apparatus comprising:
   a probe having a tip comprising a close packed array of components, said components comprising
      a light emitting die configured to irradiate said tissue;
      a detector die configured to receive radiation backscattered by said tissue;
      a shield sited between said light emitting die and said detector die to prevent leakage of optical and electrical signals from one to the other;
      an electrode configured to supply electrical signals to said tissue and to receive an electrical response from the tissue;
   said apparatus further comprising
      a controller coupled to said emitter die, said detector die and said electrode that supplies drive signals and receives the responses, said controller comprising
         a processor for said responses in combination in order to categorize said tissue, and
         a comparator for comparing the categorization of said tissue with expected tissue types from a catalogue to identify said tissue, and
      an indicator arrangement for indicating to a user the tissue type identified.

4. Apparatus for identifying tissue of claim 3 wherein said probe tip comprises a capsule with an extended lead to enable said capsule to pass into internal organs.

5. An apparatus as claimed in one of claims 3, or 4, wherein said electrode is a kidney-shaped electrode in the probe tip.

6. Apparatus as claimed in any one of claims 3 or 4, further comprising
   a circuit that feeds current to the light emitting die in the probe tip
   said detector die having wiring that is shielded electrically by a conductive metal surface mounted in close proximity to the wiring, wherein said surface reduces the capacitive coupling of the wiring to said circuit and wherein said surface further reduces the capacitive coupling to a patient during an examination with the apparatus thereby reducing the amount of cross coupling and electrical interference.

7. An apparatus as claimed in one of claims 3 or 4, in which
   said light emitting die comprises
      an LED that receives a current and output radiation in response to the current and the apparatus further comprises
   means to adjust signals received from the detector die, said means to adjust comprising
      means to measure a voltage drop to determine the temperature of the LED and means to calculate from said measured voltage drop a correction for the radiation output from the LED.

8. Apparatus for identifying tissue which is suspected of being physiologically changed as a result of precancerous or cancerous activity, said apparatus comprising:

a probe having a tip comprising a close packed array of components, said components comprising
at least one emitter comprising a light emitting die, said light emitting die configured to irradiate said tissue;
at least one detector comprising a detector die, said detector die configured to receive that radiation after it has been backscattered by said tissue;
a shield sited between said at least one emitter and said at least one detector to prevent leakage of optical and electrical signals from one to the other;

said apparatus further comprising
a controller coupled to said at least one emitter and said at least one detector that supplies drive signals and receives responses, said controller comprising
a processor for responses in combination in order to categorize said tissue, and
a comparater for comparing the categorization of said tissue with expected tissue types from a catalogue so as to identify said tissue, and
an indicator for indicating to a user the tissue type identified.

a circuit that feeds current to the light emitting die in the probe tip
said at least one detector having wiring that is shielded electrically by a conductive metal surface mounted in close proximity to the wiring, wherein said surface reduces the capacitive coupling of the wiring to said circuit and wherein said surface further reduces the capacitive coupling to a patient during an examination with the apparatus thereby reducing the amount of cross coupling and electrical interference.

9. The apparatus for identifying tissue of claim 8 further comprising an amplifier in close proximity to said at least one detector.

10. Apparatus as claimed in any one of claims 1, 2, or 9 further comprising a circuit that feeds current to the light emitting die in the probe tip
said at least one detector having wiring that is shielded electrically by a conductive metal surface mounted in close proximity to the wiring, wherein said surface reduces the capacitive coupling of the wiring to said circuit and wherein said surface further reduces the capacitive coupling to a patient during an examination with the apparatus thereby reducing the amount of cross coupling and electrical interference.

11. An apparatus as claimed in one of claims 1, 2, 9, or 8, in which
each emiter comprises
an LED that receives a current and outputs radiation in response to the current and the apparatus further comprises
means to adjust signals received from the at least one detector, said means to adjust comprising
means to measure a voltage drop to determine the temperature of the LED and
means to calculate from said measured voltage drop a correction for the radiation output from the LED.

12. Apparatus for identifying tissue which is suspected of being physiologically changed said apparatus comprising:

a probe having a tip comprising a close packed array of components, said components comprising
at least one LED that receives a current and outputs radiation in response to the current to irradicate said tissue;
at least one detector configured to receive that radiation after it has been backscattered by said tissue and to provide signals;
a shield between said at least one LED and said at least one detector to prevent leakage of radiation and electrical signals from one to the other;

said apparatus further comprising
means to adjust signals provided by the detectors, said means to adjust comprising
means to measure a voltage drop to determine the temperature of the at least one LED, and
means to calculate a correction for radiation output from the at least one LED
a controller coupled to said at least one LED and said at least one detector, said controller comprising
a processer for said responses in combination in order to categorize said tissue,
a comparater for comparing the categorization of said tissue with expected tissue types from a catalogue so as to identify said tissue, and
an indicator arrangement for indicating to a user the tissue type identified.

13. The apparatus for identifying tissue of claim 12 further comprising an amplifier in close proximity to said at least one detector.

* * * * *